(12) United States Patent
Chen et al.

(10) Patent No.: US 9,315,800 B2
(45) Date of Patent: Apr. 19, 2016

(54) METHOD FOR ISOLATING NUCLEIC ACIDS AND COMPOSITION USED THEREFOR

(71) Applicant: Industrial Technology Research Institute, Hsinchu (TW)

(72) Inventors: Yi-Chang Chen, Taipei (TW); Jane S-C Tsai, Taipei (TW)

(73) Assignee: Industrial Technology Research Institute, Hsinchu (TW)

( * ) Notice: Subject to any disclaimer, the term of this patent is extended or adjusted under 35 U.S.C. 154(b) by 56 days.

(21) Appl. No.: 13/963,699

(22) Filed: Aug. 9, 2013

(65) Prior Publication Data

US 2014/0046050 A1 Feb. 13, 2014

Related U.S. Application Data

(60) Provisional application No. 61/681,183, filed on Aug. 9, 2012.

(30) Foreign Application Priority Data

Dec. 28, 2012 (TW) .............................. 101150888 A

(51) Int. Cl.
| | |
|---|---|
| C07H 21/00 | (2006.01) |
| C12N 15/10 | (2006.01) |
| C07H 1/06 | (2006.01) |
| C07H 1/08 | (2006.01) |

(52) U.S. Cl.
CPC .............. *C12N 15/1003* (2013.01); *C07H 1/06* (2013.01); *C07H 1/08* (2013.01); *C12N 15/1013* (2013.01)

(58) Field of Classification Search
None
See application file for complete search history.

(56) References Cited

U.S. PATENT DOCUMENTS

| | | | |
|---|---|---|---|
| 5,234,809 A * | 8/1993 | Boom et al. ................. | 435/91.2 |
| 6,218,531 B1 | 4/2001 | Ekenberg | |
| 6,749,756 B1 | 6/2004 | Curran et al. | |
| 6,815,541 B1 | 11/2004 | Usui et al. | |
| 6,821,757 B2 | 11/2004 | Sauer et al. | |
| 6,825,043 B1 | 11/2004 | Curran et al. | |
| 7,173,124 B2 | 2/2007 | Deggerdal et al. | |
| 7,364,908 B2 | 4/2008 | Curran et al. | |
| 7,977,102 B2 | 7/2011 | Schmidt et al. | |
| 8,034,570 B2 | 10/2011 | Becker et al. | |
| 2002/0042055 A1 | 4/2002 | Affholter | |
| 2003/0078412 A1 | 4/2003 | Simms | |
| 2005/0042660 A1 | 2/2005 | Hall, Jr. et al. | |
| 2005/0164260 A1 * | 7/2005 | Chen ................................ | 435/6 |
| 2005/0233333 A1 | 10/2005 | Chomczynski | |
| 2007/0037933 A1 | 2/2007 | Kurth et al. | |
| 2007/0259359 A1 | 11/2007 | Briman et al. | |
| 2009/0035761 A1 | 2/2009 | Danenberg et al. | |
| 2011/0076735 A1 | 3/2011 | Jovanovich et al. | |
| 2012/0219648 A1 | 8/2012 | Medasani et al. | |
| 2012/0270332 A1 * | 10/2012 | Wimberger-Friedl et al. ............................. | 436/177 |
| 2013/0131701 A1 | 5/2013 | Komlos et al. | |
| 2014/0087361 A1 | 3/2014 | Dobbelaer et al. | |

FOREIGN PATENT DOCUMENTS

| | | |
|---|---|---|
| CN | 1042658 A | 6/1990 |
| CN | 1997740 A | 7/2007 |
| CN | 102481328 A | 5/2012 |
| CN | 103118713 A | 5/2013 |
| CN | 103518132 A | 1/2014 |
| EP | 0544824 B1 | 6/1997 |
| TW | 200909794 A | 3/2009 |

OTHER PUBLICATIONS

Berensmeir Appl. Microbiol. Biotechnol. (2006), vol. 73, pp. 495-504.*

Chinese Office Action and Search Report for Chinese Application No. 201310170889.3, dated Nov. 14, 2014.

* cited by examiner

*Primary Examiner* — Patrick Lewis
(74) *Attorney, Agent, or Firm* — Birch, Stewart, Kolasch & Birch, LLP

(57) ABSTRACT

The disclosure provides a composition and method for isolating nucleic acids, in which the composition includes at least one halocarbon, at least one salt and at least one surfactant. Mixing the composition and a biosample to form a homogenized solution, nucleic acids in the solution can be easily isolated with a simple treatment and good yield.

20 Claims, 5 Drawing Sheets

METHOD FOR ISOLATING NUCLEIC ACIDS AND COMPOSITION USED THEREFOR

CROSS REFERENCE TO RELATED APPLICATIONS

This application claims the priority of Taiwan Patent Application No. 101150888, filed Dec. 28, 2012, which claims the priority of U.S. Provisional Application No. 61/681,183, filed Aug. 9, 2012, the disclosure of which is hereby incorporated by reference herein in its entirety.

TECHNICAL FIELD

The technical field relates to a method for isolating nucleic acids and a composition used therefore.

BACKGROUND

While molecular diagnostics is transforming the practice of medicine, current molecular procedures are time-consuming. Complex sample preparation procedures have been identified as among the bottlenecks in achieving rapid and high-throughput molecular diagnostics. Currently available reagents for isolating nucleic acids generally involve more than one step and require the use of more than one test tube. Therefore, these commercially available reagents take longer sample preparation time and have higher risks for sample contamination. Furthermore, these commercial reagents utilize specialized formulations for specified types of biosamples.

Therefore, novel methods and reagents for reducing the risk of sample contamination while increasing the purity of the isolated nucleic acids in fewer steps in a short period of time are in demand.

SUMMARY

One embodiment of the disclosure provides a composition for isolating a nucleic acid, which comprises at least one halocarbon, at least one salt and at least one surfactant. In addition, the composition contains 1~70% by weight of the halocarbon based on the total weight of the composition.

Another embodiment of the disclosure provides a method for isolating a nucleic acid, comprising mixing a composition and a biosample to form a homogenized solution and isolating the nucleic acids from the homogenized solution. Herein, the composition comprises at least one halocarbon, at least one salt and at least one surfactant and contains 1~70% by weight of the halocarbon based on the total weight of the composition.

BRIEF DESCRIPTION OF THE DRAWINGS

The present invention can be more fully understood by reading the subsequent detailed description and examples with references made to the accompanying drawings, wherein.

DETAILED DESCRIPTION

Figure 1A:
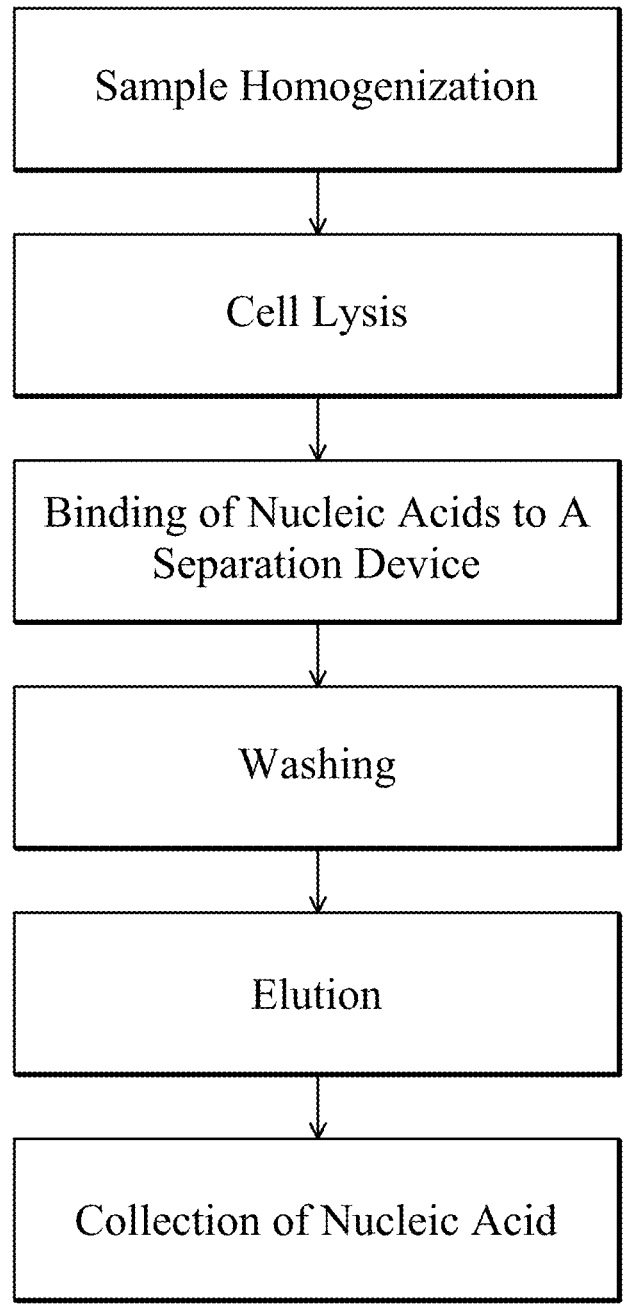
FIG. 1A is a schematic view showing conventional steps for nucleic acid isolation.

In the following detailed description, for purposes of explanation, numerous specific details are set forth in order to provide a thorough understanding of the disclosed embodiments. It will be apparent, however, that one or more embodiments may be practiced without these specific details. In other instances, well-known structures and devices are schematically shown in order to simplify the drawing.

It has been well known that nucleic acid isolation conventionally requires the following steps: sample homogenization, cell lysis, binding of nucleic acid molecules to a separation device, washing and elution of the nucleic acid molecules bound on the separation device (FIG. 1A).

The conventional nucleic acid isolation is performed in more than one test tube with certain risks of sample contamination, and also, the operating period is therefore increased. In addition, conventional isolation uses toxic solvents, such as phenol, chloroform, etc., which is unfriendly to operators and environment. It has also been noted that the conventional isolation has limits on types of samples and sample sizes, such as 10~40 mg, for obtaining higher purity.

Perfluorocarbons have been used as quenching liquids for electronic products and are widely used in the electronic industry. However, in developing novel methods and compositions for nucleic acid isolation, inventors have been well aware that perfluorocarbons are capable of eliminating the interference of proteins and possess chemical stability in high- or low-temperature conditions. Perfluorocarbons are not left in the final step of isolation. Thus, for nucleic acid isolation, use of perfluorocarbon can improve the purity of the isolated nucleic acids and simplify the operating steps.

The composition given in the disclosure is superior to the conventional reagents based on the improved purity of the isolated nucleic acids, reduced operating steps and periods, extensive applicability on various sample types and non-toxicity to humans and environment.

Figure 1B:
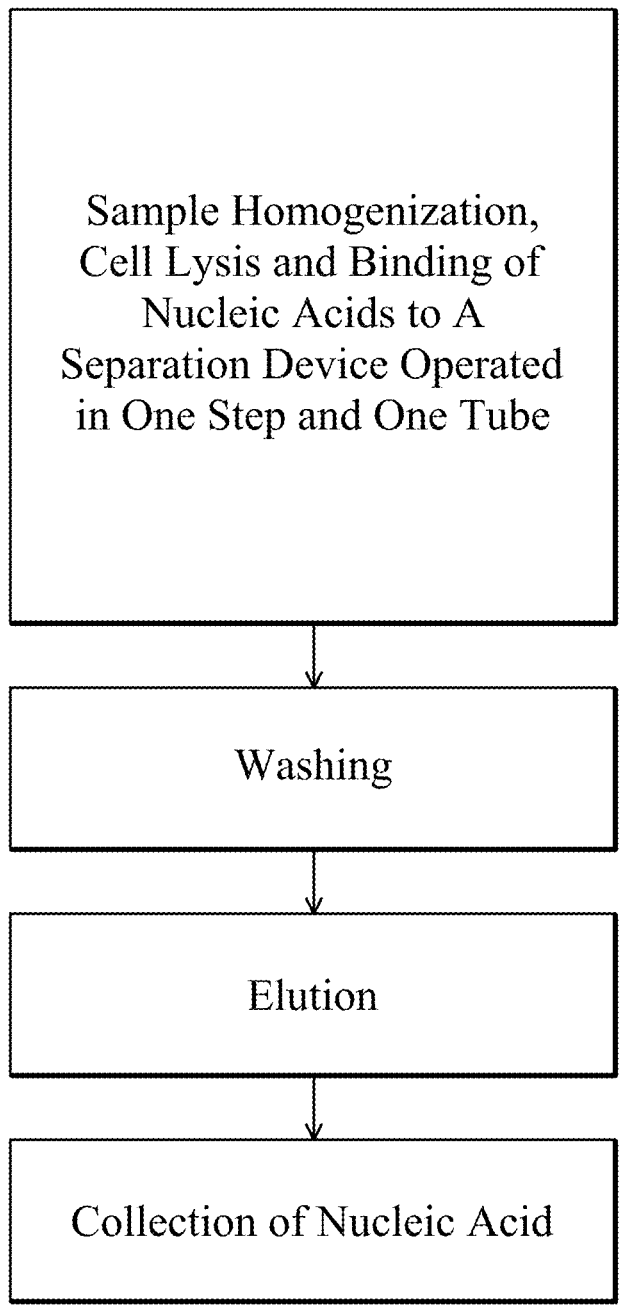
FIG. 1B is a schematic view showing the steps for isolating nucleic acid according to one embodiment of the disclosure.

According to the present invention, the use of the composition given in the disclosure allows the entire isolation to be performed in one step and in one tube (FIG. 1B) with no need for several steps in different tubes for sample homogenization, cell lysis, and binding of nucleic acid molecules to the separation device, as conventional nucleic acid isolation does. Thus, the use of the composition given in the disclosure can reduce the risk of sample contamination and shrink operating periods and steps. Because the composition is free of toxic solvents like phenols or chloroforms, use of the composition given in the disclosure for nucleic acid isolation can reduce toxicity to operators and the environment. In addition, the composition given in the disclosure can be extensively applied for a variety of tissue types as described in the following Examples, with excellent yields of nucleic acids. The operable sample size therefore enlarges to approximately 10 μg~100 mg. Compared to conventional nucleic acid isolation, the present invention provides a composition and method with improved purity, reduced operating steps, decreased purified periods, extensive application to sample types and sizes and non-toxicity to human beings and the environment.

The composition, according to one embodiment of the disclosure, comprises at least one halocarbon, at least one salt and at least one surfactant.

The halocarbons disclosed herein may comprise fluorocarbons, chlorocarbons, bromocarbons or the like. In one example, perfluorocarbon is used as the halocarbons in the composition according to the present invention. Perfluorocarbons have been used as quenching liquids for electronic products and are widely used in the electronic industry. However, in developing novel methods and compositions for nucleic acid isolation, inventors have been well aware that perfluorocarbons are capable of eliminating the interference of proteins and possess chemical stability in high- or low-temperature conditions. In addition, perfluorocarbons are not left in the final step of isolation. Thus, the purity of the isolated nucleic acids can be therefore improved.

In one embodiment of the disclosure, the perfluorocarbon may comprise $C_1$~$C_{12}$ perfluoroalkane, such as tetrafluoromethane, hexafluoroethane, perfluropropane, perfluorobutane, perfluoropentane, perfluorohexane, perfluoroheptane or perfluorooctane; or $C_3$~$C_{12}$ perfluorocycloalkane, such as perfluorocyclopropane, perfluorocyclobutane, perfluorocyclopentane, perfluorocyclohexane or perfluorocyclooctane.

In one embodiment of the disclosure, the salt may comprise alkali salts, alkali earth salts, guanidine salts or a combination thereof. The alkali salt may comprise lithium salts, sodium salts or potassium salts, such as lithium chloride (LiCl), sodium chloride (NaCl) or potassium chloride (KCl), etc. The alkali earth salts may comprise magnesium salts or calcium salts, such as magnesium chloride or calcium carbonate, etc. The guanidine salts may comprise guanidinium chloride (GuCl) or guanidine isothiocyanate (GuSCN), etc.

In one embodiment of the disclosure, the surfactant can be a surfactant known for nucleic acid isolation and there is no specific limitation. For example, the surfactant can be polysorbate, like Tween 20 or Tween 80; polyethylene glycol p-(1,1,3,3-tetramethylbutyl)-phenyl ether, like Triton X-100; or a combination thereof.

In one embodiment of the disclosure, the composition for isolating nucleic acids may contain 1~70% by weight of the halocarbon based on the total weight of the composition. In one example, the composition for isolating nucleic acids may contain 10~60% by weight of the halocarbon based on the total weight of the composition. In another example, the composition for isolating nucleic acids may contain 20~50% by weight of the halocarbon based on the total weight of the composition.

In one embodiment, the composition for isolating nucleic acids may contain 0.01~10% by weight of the surfactant based on the total weight of the composition. In one example, the composition for isolating nucleic acids may contain 0.1~8% by weight of the surfactant based on the total weight of the composition. In one example, the composition for isolating nucleic acids may contain 1~5%, by weight of the surfactant based on the total weight of the composition.

In one embodiment, the composition for isolating nucleic acids may contain 5~80% by weight of the salt based on the total weight of the composition. In one example, the composition for isolating nucleic acids may contain 20~70% by weight of the salt based on the total weight of the composition. In one example, the composition for isolating nucleic acids may contain 30~60% by weight of the salt based on the total weight of the composition. In one example, a mixture of lithium chloride (LiCl) and guanidine isothiocyanate (GuSCN) is used as the salt in the composition for isolating nucleic acids. In this example, lithium chloride (LiCl) is 14.83~63.58% by weight and guanidine isothiocyanate (GuSCN) is 11.816~70.896% by weight, based on 100% by weight of the salt.

In one embodiment of the disclosure, the composition for isolating nucleic acids may further comprise magnetic particles. The magnetic particle may be magnetic particles conventionally used in the biotechnical field without specific limitation, such as ferrite nanoparticles or ultra-small superparamagnetic iron oxide (USPIO) nanoparticles.

In one embodiment, the disclosure provides a method for isolating nucleic acid, comprising the following steps: mixing a composition and a biosample to form a homogenized solution, in which the composition comprises at least one halocarbon, at least one salt and at least one surfactant, and isolating nucleic acids from the homogenized solution.

The halocarbons, salts and surfactants have been described above. As mentioned earlier, the method for isolating nucleic acid given in the disclosure is superior to the conventional ones on the grounds of high purity, reduced operating steps and periods, extensive application of sample types and sizes and non-toxicity to human beings and the environment.

In one embodiment of the disclosure, the method is applicable to a variety of sample types, such as cells, tissues, blood, sera, urine, amniotic fluid, lymph, saliva, feces or a combination thereof.

The method given in the disclosure comprises isolation of nucleic acids from the homogenized solution. In one example, the isolation of nucleic acids may be performed with centrifugation, chromatography or the like. In another example, the isolation of nucleic acids may be performed with magnetic purification. In this example, the composition used for isolating nucleic acids comprises at least one halocarbon, at least one salt, at least one surfactant and magnetic particles. As mixing the lysed biosample with the composition, the nucleic acids of the biosample binds to the magnetic particles in the composition and the magnetic particles are subsequently collected with a magnetic collection device, like magnetic stage. The collected magnetic particles are eluted with specific solvents thereafter to isolate and purify the nucleic acids bound on the magnetic particles.

The magnetic particles may be magnetic particles conventionally used in biotechnical field without specific limitation, such as ferrite nanoparticles or ultra-small superparamagnetic iron oxide (USPIO) nanoparticles. The magnetic collection device and elution solvents can be suitably adopted depending on the characteristics of the magnetic particles, the features of the nucleic acids for isolation or the like. The magnetic collection device may comprise a magnetic plate, ring magnet or the like. The elution solvent may be commercial elution buffers, such as sodium dihydrogen phosphite ($NaH_2PO_3$), urea, thiourea, guanidinium chloride (GuCl), tris(hydroxymethyl)amino methane (Tris HCl), or a combination thereof.

In one example, the method for isolating nucleic acids given in the disclosure further comprises a washing step before isolating nucleic acids, for removing protein impurities from the homogenized solution. The washing step may be performed with commercial washing buffers, such as double-distilled water ($ddH_2O$), ethanol or a combination thereof.

The magnetic particles, elution solvents and washing buffers in the disclosure can be commercial reagents or kits without specific limitation. The reagents and kits can be suitably adopted according to the features of the biosample for reaching high purity and isolation efficacy.

The composition and method given in the disclosure simplify the isolation of nucleic acid from a biosample, such as single-stranded nucleic acids, double-stranded nucleic acids, nucleic acid fragments or a combination thereof. As mentioned earlier, the composition and method given herein is applicable to extensive sample types and sample sizes.

Example 1

Nucleic Acid Isolation

1. Nucleic Acid Isolation with the Composition in One Embodiment of the Disclosure
(1) Preparation of Composition (1)
500 µl of perfluorohexane (Fluorinert™), 190.75 µl of a mix solution consisting of 4.5M LiCl and 5M GuCl and 1 µl of Triton X-100 were mixed to form Composition (1). Composition (1) would be used as lysis buffers in the next steps.
(2) Nucleic Acid Isolation from Tissues
1 mg of mouse liver tissues were added into a grind tube which contained Composition (1) as lysis buffers. The grind tube was ground for about 5 minutes and washed with 1000 µl of buffers (a mixture of 300 µl of 3.5M LiCl and 700 µl of 70% ethanol) 10 times. 20 µl of magnetic beads (Ambion MagMax total RNA pure beads) were then added to the same tube and mixed uniformly.

The RNA-binding magnetic beads in the mixed solution were separated with magnetic stage (Ambion). The beads were eluted 20 times per min with diethyl pyrocarbonate (DEPC) aqueous solution. A purified sample (named "ITRI sample") was obtained. The operating period by using Composition (1) for nucleic acid isolation took about 20 minutes in total.

2. Nucleic Acid Isolation with Commercial Reagents
1 mg of commercial Qiagen RNAeasy® buffers and 600 µl of RNA stabilization reagents were added to a tube and vortexed for about 20~40 seconds.

1 mg of mouse liver tissues were added to the same tube for another 10 minutes. 500 µl of commercial Qiagen RNAeasy® lysate buffers were subsequently added to the same tube and mixed uniformly. The mixed solution was then moved to centrifuged tubes in batches and centrifuged at full speed for 5 minutes. The centrifuged solution was then moved to a new tube. 350 µl of commercial RLT buffers were added to the tube and then vortexed and centrifuged at 300 g for 5 minutes to break cells. The solution in the tube was aspirated and pumped 20 times. The lysis steps herein were repeated 5 times.

After the lysis treatment, the solution was moved to another new tube and centrifuged at full speed for 2 minutes. The supernatant was removed. The tube was vortexed for 30 seconds and washed with 700 µl of 70% ethanol. The tube was moved to a spin column for centrifugation. The steps herein after the lysis treatment were repeated twice.

Thereafter, 700 µl of commercial RW1 buffers were added to the treated solution and centrifuged at full speed for 2 minutes. 500 µl of RPE buffers were then added and moved to a spin column for centrifugation. The step was repeated twice. The treated solution was changed to another new tube and the supernatant was removed. The centrifugation was repeated. Thereafter, 50 µl of RNA DEPC water was added to the treated solution. A purified sample (named "Qiagen sample") with Qiagen RNAeasy® reagent was obtained. The operating period by using Qiagen RNAeasy® reagent for nucleic acid isolation took about 120 minutes in total.

3. Analyses of Isolated RNA Samples

Figure 2:
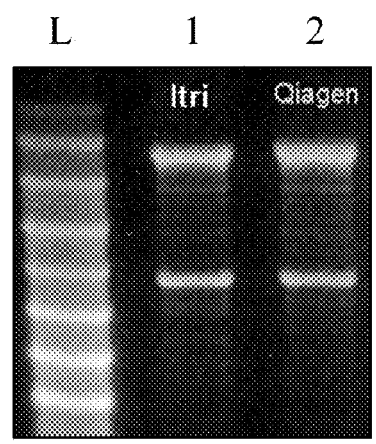
FIG. 2 is a gel electrophoresis photograph showing the nucleic acids isolated from a biosample according to one embodiment of the disclosure, in which the same biosample isolated with a commercial reagent (Qiagen) is listed on the same gel for reference.

The ITRI sample (isolated with Composition (1)) and Qiagen sample (isolated with Qiagen RNAeasy® reagent) was analyzed by gel electrophoresis (75V, TAE gel). The gel electrophoresis photograph was shown in FIG. 2. In FIG. 2, Lane L showed markers, Lane 1 showed the ITRI sample and Lane 2 showed the Qiagen sample.

The total RNAs and the absorbance at $OD_{260}$, $OD_{280}$ and $OD_{230}$ of the ITRI sample and Qiagen sample were tested with a spectrophotometer (NanoDrop®). The ratios of $OD_{260}/OD_{280}$ and $OD_{260}/OD_{230}$ were calculated and listed in Table 1.

TABLE 1

|  | Total RNA (µg/mg) | $OD_{260}/OD_{280}$ | $OD_{260}/OD_{230}$ |
| --- | --- | --- | --- |
| ITRI Sample | 6.04 | 2.08 | 2.18 |
| Qiagen Sample | 5.99 | 1.95 | 2.16 |

According to FIG. 2 and Table 1, the purity of nucleic acid RNA isolated with Composition (1) (ITRI sample) was not lower than that isolated with commercial Qiagen RNAeasy® reagents (Qiagen sample), but the operating period was significantly reduced and the operating steps were simplified as well. This result reveals that the composition given in the disclosure is superior to the commercial reagents in the aspect of isolation of nucleic acid.

Example 2

Isolation of Nucleic Acids from Various Tissue Types

1. Preparation of Composition (2)
500 µl of perfluorohexane (Fluoriner™), 169.5 µl of 4M LiCl and 700 µl of ethanol were mixed uniformly to form the Composition (2). Composition (2) would be used as lysis buffer in the next steps.

2. Isolation of RNA from Various Mouse Visceral Organs
0.1 mg of mouse liver tissues, heart tissues, spleen tissues or kidney tissues were respectively added to a grind tube which contained Composition (2) as lysis buffers. Each of the grind tubes was ground for about 5 minutes and washed with 1000 µl buffer (a mixture of 300 µl of 4M LiCl and 700 µl of 70~90% ethanol) 10 times. 20 µl of magnetic beads (Ambion) was then added to each tube and mixed uniformly. The RNA-binding magnetic beads in the mixed solution were separated with magnetic stage (Ambion). The beads were eluted 20 times per min with DEPC aqueous solution. The purified RNA solution was collected and analyzed by gel electrophoresis (75V, TAE gel) as shown in FIG. 3.

Figure 3:
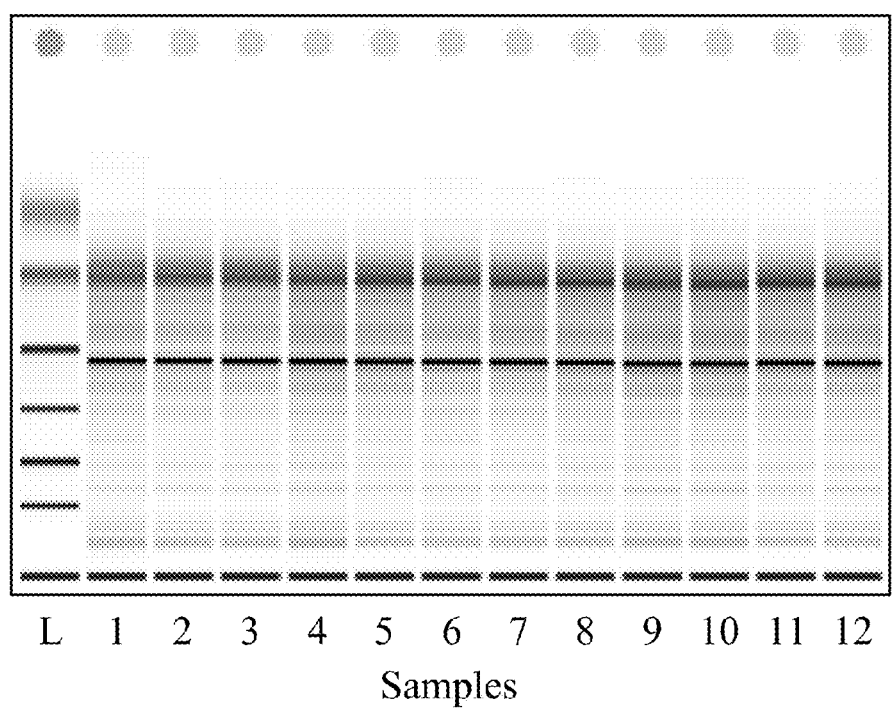
FIG. 3 is a gel electrophoresis photograph showing the RNA samples isolated from various tissue types according to one embodiment of the disclosure.

In FIG. 3, Lane L showed markers, Lanes 1, 2 and 3 showed the heart tissue samples, Lanes 4, 5 and 6 showed the spleen tissue samples, Lanes 7, 8, 9 and 10 showed the liver tissue samples and Lanes 11 and 12 showed the kidney tissue samples.

Meanwhile, the RNA samples were further analyzed RNA integrity number (RIN) with Agilent 2100®. The results were shown in Table 2.

TABLE 2

| | Tissue types | | | | | | | | | | | |
|---|---|---|---|---|---|---|---|---|---|---|---|---|
| | heart | | | spleen | | | liver | | | kidney | | |
| Lane No. | 1 | 2 | 3 | 4 | 5 | 6 | 7 | 8 | 9 | 10 | 11 | 12 |
| RIN | 6 | 7.80 | 8 | 7.30 | 7.70 | 7.80 | 7.80 | 7.50 | 7.50 | 7.50 | 7.60 | 7.70 |

According to FIG. 3 and Table 2, it shows that the composition given in the disclosure is applicable for isolation of nucleic acids from various tissue types and the purity of the isolated nucleic acids does not lower down.

Example 3

Isolation with Centrifugation

1. Preparation of Composition (3)

500 μl of perfluorohexane (Fluorinert™), 169.5 μl of 4M LiCl and 700 μl of ethanol were mixed uniformly to form the Composition (3). Composition (3) would be used as lysis buffer in the next steps.

Figure 4:
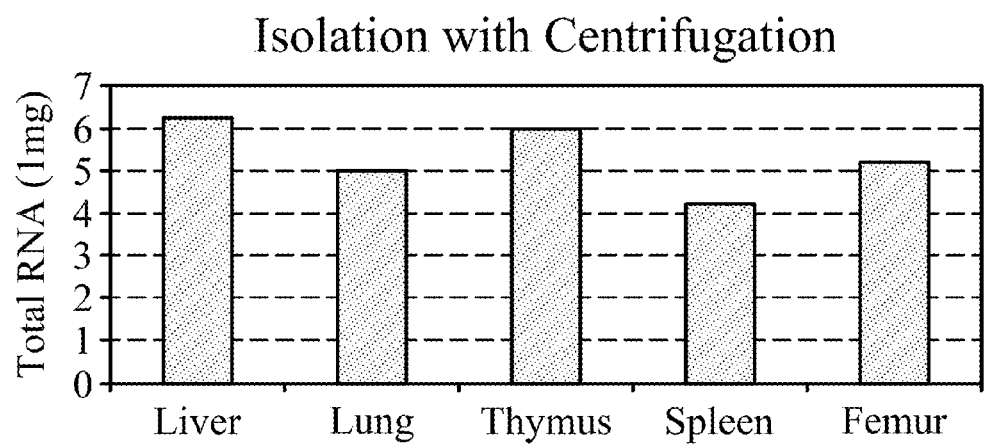
FIG. 4 is a histogram showing the total RNAs isolated from various tissue types with centrifugation according to one embodiment of the disclosure.
Figure 6:
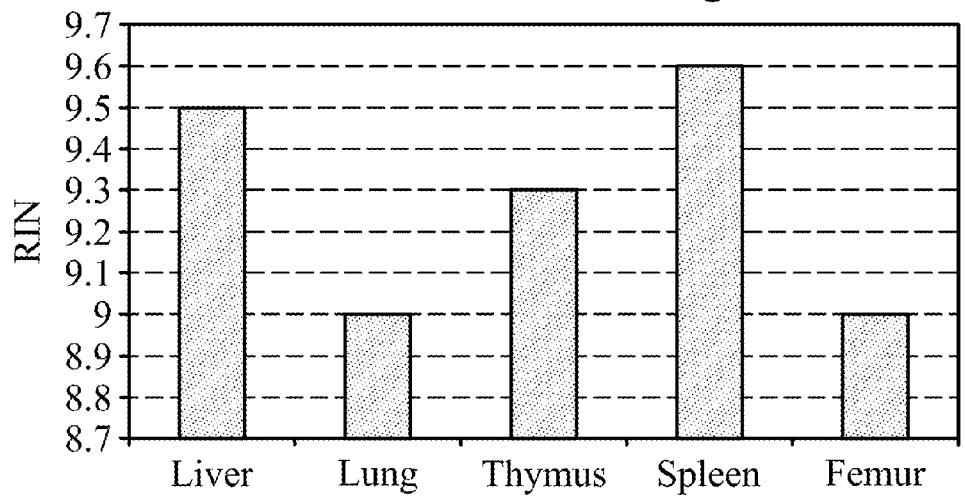
FIG. 6 is a histogram showing the RIN of the RNAs isolated from various tissue types with centrifugation according to one embodiment of the disclosure.

2. Isolation with Centrifugation 0.1 mg of mouse liver tissues, lung tissues, thymus tissues, spleen tissues or femur tissues were respectively added to a grind tube which contained Composition (3) as lysis buffers. Each of the grind tubes was ground for about 5 minutes and washed with 1000 μl buffers (a mixture of 300 μl of 4M LiCl and 700 μl of 70~90% ethanol) 10 times. The treated solution was centrifuged at 1000 rpm (centrifuge: Eppendorf) to obtain isolated RNA solution. The isolated RNA solution was analyzed the content of total RNAs as shown in FIG. 4 and the RIN with Agilent 2100® as shown in FIG. 6.

Example 4

Isolation with Magnetic Purification

1. Preparation of Composition (3)

500 μl of perfluorohexane (Fluorinert™), 169.5 μl of 4M LiCl and 700 μl of ethanol were mixed uniformly to form the Composition (3). Composition (3) would be used as lysis buffer in the next steps.

Figure 5:
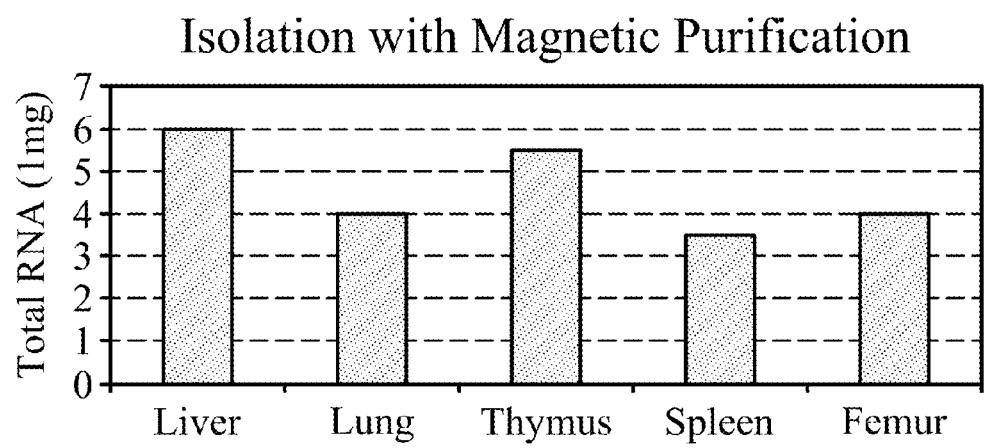
FIG. 5 is a histogram showing the total RNAs isolated from various tissue types with magnetic purification according to one embodiment of the disclosure.
Figure 7:
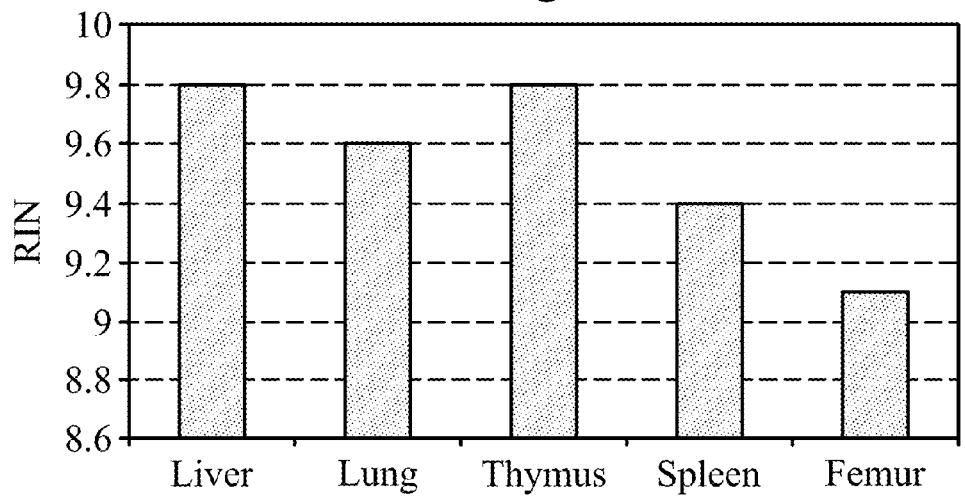
FIG. 7 is a histogram showing the RIN of the RNAs isolated from various tissue types with magnetic purification according to one embodiment of the disclosure.

2. Isolation with Magnetic Purification 0.1 mg of mouse liver tissues, heart tissues, spleen tissues or kidney tissues were respectively added to a grind tube which contained Composition (3) as lysis buffers. Each of the grind tubes was ground for about 5 minutes and washed with 1000 μl buffer (a mixture of 300 μl of 4M LiCl and 700 μl of 70~90% ethanol) 10 times. 20 μl of magnetic beads (Ambion) was then added to each tube and mixed uniformly. The RNA-binding magnetic beads in the mixed solution were separated with magnetic stage (Ambion). The beads were eluted 20 times per min with DEPC aqueous solution to obtain an isolated RNA solution. The isolated RNA solution was analyzed the content of total RNAs as shown in FIG. 5 and the RIN with Agilent 2100® as shown in FIG. 7.

According to FIGS. 4~7, it is evident that the composition given in the disclosure leads to a high purity of the isolated nucleic acids no matter what purification method is used (for instance, centrifugation or magnetic purification).

Example 5

Isolation by Using Compositions with Different Component Ratios

Compositions (4)~(10) were prepared according to Table 3 below. The isolation steps followed Example 2 and the absorbance analyses followed Example 1. The obtained ratios of $OD_{260}/OD_{280}$ and $OD_{260}/OD_{230}$ are listed in Table 3.

TABLE 3

| Composition | Perfluorohexane (w/w %) | Salts (w/w %) | Surfactant (w/w %) | ddH$_2$O (w/w %) | Yield (μg/mg) | $OD_{260}/OD_{280}$ | $OD_{260}/OD_{230}$ |
|---|---|---|---|---|---|---|---|
| (4) | 10 | 20 | 1 | 69 | 3.5 | 1.6 | 1.2 |
| (5) | 20 | 20 | 1 | 59 | 3.8 | 1.75 | 1.28 |
| (6) | 30 | 20 | 1 | 49 | 4 | 1.8 | 1.35 |
| (7) | 40 | 20 | 1 | 39 | 4.5 | 1.9 | 1.5 |
| (8) | 50 | 20 | 1 | 29 | 4.6 | 2 | 1.6 |
| (9) | 60 | 20 | 1 | 19 | 4.2 | 2.2 | 1.68 |
| (10) | 70 | 20 | 1 | 9 | 3.9 | 2 | 1.35 |

According to Table 3, it is clear that the composition given in the disclosure results in a high purity of the isolated nucleic acids no matter what the component ratios of the composition are.

It will be apparent to those skilled in the art that various modifications and variations can be made to the disclosed embodiments. It is intended that the specification and examples be considered as exemplary only, with a true scope of the disclosure being indicated by the following claims and their equivalents.

What is claimed is:

1. A composition for isolating nucleic acids, comprising
at least one perfluorocarbon,
at least one salt, and
at least one surfactant,
   wherein the composition contains 1~70% by weight of the perfluorocarbon based on the total weight of the composition, and
   wherein the perfluorocarbon comprises perfluoropentane, perfluorohexane, perfluoroheptane or perfluorooctane.

2. The composition as claimed in claim 1, wherein the salt comprises alkali salts, alkali earth salts, guanidine salts or a combination thereof.

3. The composition as claimed in claim 1, wherein the composition contains 5~80% by weight of the salt based on the total weight of the composition.

4. The composition as claimed in claim 1, wherein the surfactant comprises polysorbate, polyethylene glycol p-(1,1,3,3-tetramethylbutyl)-phenyl ether or a combination thereof.

5. The composition as claimed in claim 1, wherein the composition contains 0.01~10% by weight of the surfactant based on the total weight of the composition.

6. The composition as claimed in claim 1, wherein the composition further comprises magnetic particles.

7. The composition as claimed in claim 6, wherein the magnetic particle comprises ferrite nanoparticles, ultra-small superparamagnetic iron oxide nanoparticles or a combination thereof.

8. The composition as claimed in claim 1, wherein the nucleic acid comprises single-stranded nucleic acids, double-stranded nucleic acids, nucleic acid fragments or a combination thereof.

9. A method for isolating nucleic acid, comprising following steps: mixing the composition of claim 1 and a biosample to form a homogenized solution, and isolating nucleic acids from the homogenized solution.

10. The method as claimed in claim 9, wherein the salt comprises alkali salts, alkali earth salts, guanidine salts or a combination thereof.

11. The method as claimed in claim 9, wherein the composition contains 5~80% by weight of the salt based on the total weight of the composition.

12. The method as claimed in claim 9, wherein the surfactant comprises polysorbate, polyethylene glycol p-(1,1,3,3-tetramethylbutyl)-phenyl ether or a combination thereof.

13. The method as claimed in claim 9, wherein the composition contains 0.01~10% by weight of the surfactant based on the total weight of the composition.

14. The method as claimed in claim 9, wherein the biosample comprises cells, tissues, blood, sera, urine, amniotic fluid, lymph, saliva, feces or a combination thereof.

15. The method as claimed in claim 9, wherein the nucleic acid comprises single-stranded nucleic acids, double-stranded nucleic acids, nucleic acid fragments or a combination thereof.

16. The method as claimed in claim 9, wherein the isolation comprises centrifugation or chromatography.

17. The method as claimed in claim 9, wherein the composition further comprises magnetic particles.

18. The method as claimed in claim 17, wherein the magnetic particle comprises ferrite nanoparticles, ultra-small superparamagnetic iron oxide nanoparticles or a combination thereof.

19. The method as claimed in claim 18, wherein the isolation comprises separation of the magnetic particles and elution of nucleic acids bound on the magnetic particles.

20. The method as claimed in claim 9, further comprising a washing step to separating proteins before the isolation.

* * * * *